United States Patent
Oliveira Santos et al.

(10) Patent No.: US 11,609,102 B1
(45) Date of Patent: Mar. 21, 2023

(54) GYROSCOPE DRIFT ESTIMATION AND COMPENSATION WITH ANGLE OF ARRIVAL OF ELECTROMAGNETIC WAVES

(71) Applicant: SWORD HEALTH, S.A., Oporto (PT)

(72) Inventors: Pedro Henrique Oliveira Santos, Oporto (PT); José Carlos Coelho Alves, Oporto (PT); Pedro Miguel Simões Bastos Martins, Oporto (PT); Pedro Miguel Moreira de Sousa, Oporto (PT); Pedro Filipe Xavier Rodrigues, Oporto (PT); Márcio Filipe Moutinho Colunas, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 17/940,897

(22) Filed: Sep. 8, 2022

(30) Foreign Application Priority Data

Jun. 3, 2022 (EP) ..................................... 22398013

(51) Int. Cl.
*G01C 25/00* (2006.01)
*G01S 5/02* (2010.01)
*G01S 5/00* (2006.01)
*H04W 4/02* (2018.01)

(52) U.S. Cl.
CPC ........... *G01C 25/00* (2013.01); *G01C 25/005* (2013.01); *G01S 5/0036* (2013.01); *G01S 5/0284* (2013.01); *H04W 4/023* (2013.01)

(58) Field of Classification Search
USPC ......................................................... 702/141
See application file for complete search history.

(56) References Cited

U.S. PATENT DOCUMENTS

| | | | | |
|---|---|---|---|---|
| 2010/0121601 | A1* | 5/2010 | Eckert | F41G 7/007 701/500 |
| 2019/0166453 | A1* | 5/2019 | Edge | G01S 5/06 |
| 2021/0076350 | A1* | 3/2021 | Yang | G01S 3/50 |
| 2022/0264251 | A1* | 8/2022 | Wang | H04W 4/029 |
| 2022/0303680 | A1* | 9/2022 | Ahmed | H04W 76/14 |

FOREIGN PATENT DOCUMENTS

| | | |
|---|---|---|
| EP | 3804420 B1 | 12/2021 |
| WO | WO-2019243438 A1 | 12/2019 |

* cited by examiner

*Primary Examiner* — Paul D Lee
(74) *Attorney, Agent, or Firm* — Wilson Sonsini Goodrich & Rosati

(57) ABSTRACT

A method including: wirelessly transmitting and receiving data packets between first and second apparatuses; determining first and second angles of arrival at each apparatus for electromagnetic waves of the received data packets; providing first and second directions of arrival corresponding to the angles of arrival; converting the first and second directions into a global frame; projecting the first and second converted directions onto a horizontal plane; and computing a first drift estimate for a gyroscope or IMU of the first apparatus relative to the second apparatus, and/or computing a second drift estimate for a gyroscope or IMU of the second apparatus relative to the first apparatus, the first drift estimate being based on a difference between the projected second direction and a mirrored projected first direction, and the second drift estimate being based on a difference between the projected first direction and a mirrored projected second direction.

20 Claims, 3 Drawing Sheets

GYROSCOPE DRIFT ESTIMATION AND COMPENSATION WITH ANGLE OF ARRIVAL OF ELECTROMAGNETIC WAVES

CROSS-REFERENCE TO RELATED APPLICATIONS

This application claims the benefit of European Application No. 22398013.7, filed on Jun. 3, 2022, which is incorporated by reference herein in its entirety.

TECHNICAL FIELD

The present disclosure relates to the technical field of inertial measurements units, IMUs. More particularly, it relates to the estimation of the drift that gyroscopes of IMUs accumulate over time so that the same may be compensated for, or at least a heading of measurements of the IMUs can have the drift of the gyroscopes compensated for, relative to the measurements of other gyroscopes or IMUs.

BACKGROUND

IMUs include inertial sensors that measure e.g. orientations, angular velocities, accelerations, magnetic fields, forces, etc. Many industries employ the sensors and, especially, the IMUs in their applications to keep track of these measurements. Motion tracking systems, navigation systems, control systems, etc. include IMUs for an adequate operation.

The main drawback of IMUs is that their sensors are prone to drifts and disturbances, which introduce errors in the measurements. Gyroscopes, which are one of the common sensors in IMUs, are subject to drift as a result of both DC offset and electrical noise in its components. As time goes on, the drift in the gyroscopes tends to increase and so does the error in the measurements they provide.

One way the drift of the gyroscopes is reduced is with the frequent calibration of the gyroscope by using data about the orientation of the IMUs. The data is generally external to the device, i.e. it is data provided by a device different from the IMU. The orientation indicated in such data can be used to adjust the orientation that the gyroscope is measuring. After each such adjustment, the gyroscope again starts to provide orientation measurements with an increasing error due to the drift, so the calibration, i.e. the orientation adjustments, must be effect frequently to reduce the error in the measurements they provide.

The data for the calibration of the gyroscope may be provided by a number of devices or sources of information, each of which has its own level of accuracy, and the obtention of the data being more or less complex. In this sense, there is an interest in finding a source of data that serves to provide an accurate estimation of the drift of gyroscopes so that the error they introduce in heading values provided by the IMUs can be compensated for.

SUMMARY

Some aspects of the disclosure relates to a method comprising:

wirelessly transmitting one or more first data packets from a first apparatus to a second apparatus, each of the first and second apparatuses comprising:
  at least one antenna array, each antenna array of the at least one antenna array being arranged to make an angle of arrival of packets wirelessly received measurable with respect to a respective plane; and
  an inertial measurement unit, IMU, comprising both a gyroscope and an accelerometer;

wirelessly receiving one or more second data packets at the first apparatus from the second apparatus, the one or more second data packets comprising: measurements of the IMU of the second apparatus, and angle of arrival data indicative of a first angle of arrival with which the second apparatus has wirelessly received the one or more first data packets, the first angle of arrival comprising angle information with respect to each plane that the at least one antenna array of the second apparatus makes the angle of arrival measurable;

determining, by the first apparatus, the second angle of arrival with which the first apparatus has wirelessly received the one or more second data packets when the at least one antenna array of the second apparatus is arranged to make the first angle of arrival of the one or more first data packets at least measurable with respect to a horizontal plane based on both an orientation of the second apparatus and antenna array arrangement data of the second apparatus and further when the at least one antenna array of the first apparatus is arranged to make the second angle of arrival of the one or more second data packets at least measurable with respect to a horizontal plane based on both an orientation of the first apparatus and antenna array arrangement data of the first apparatus, the orientation of the first and second apparatuses comprising the measurements of the IMU of the respective apparatus, and the second angle of arrival comprising angle information with respect to each plane that the at least one antenna array of the first apparatus makes the angle of arrival measurable;

providing, by the first apparatus, first and second directions of arrival, the first direction being defined by the first angle of arrival and the second direction being defined by the second angle of arrival;

converting, by the first apparatus, the first direction into a global frame by applying a first transformation thereto based on the orientation of the first apparatus, and converting the second direction into the global frame by applying a second transformation thereto based on the orientation of the second apparatus;

projecting, by the first apparatus, both the first and second converted directions onto a horizontal plane; and computing, by the first apparatus, a first drift estimate for the gyroscope or IMU of the first apparatus relative to the second apparatus, and/or computing a second drift estimate for the gyroscope or IMU of the second apparatus relative to the first apparatus, the first drift estimate being based on a difference between the projected second direction and a mirrored projected first direction, and the second drift estimate being based on a difference between the projected first direction and a mirrored projected second direction.

The method enables estimation of the drift that the gyroscope and/or IMU of one or both of the first and second apparatuses introduces in the measurements thereof relative to the measurements of the gyroscope and/or IMU of the other apparatus.

Both apparatuses are capable of establishing a horizontal plane by way of the measurements provided by its respective accelerometer and/or IMU. The horizontal plane is defined by a normal vector that is vertical, and e.g. the gravity acceleration provided by the accelerometer and/or IMU have/has a vertical direction. In this sense, the second apparatus may preferably, but not necessarily, arranged such that its at least one antenna array makes an angle of arrival of packets wirelessly received by the second apparatus at least measurable with respect to a plane having a normal vector perpendicular to a plane of a floor above which the second apparatus is located, and said arrangement is preferably maintained at least during a period of time comprising the steps of wirelessly transmitting the one or more first data packets and wirelessly receiving the one or more second data packets.

The first apparatus estimates the drift of either gyroscope or IMU by means of the wireless communications between the first and second apparatuses. The relative orientation of one apparatus with respect to the other, particularly of their respective antenna arrays, is determinable from the angle of arrival of the electromagnetic waves with data packets that each apparatus receives from the other.

Each apparatus radiates electromagnetic waves corresponding to radiofrequency signals with data packets therein, and the other apparatus captures the waves. Then, the apparatus determines the angle of arrival of the waves owing to the different phase and/or time of arrival with which each antenna in the at least one antenna array captures the waves. By processing the angle of arrival with which each apparatus has captured the electromagnetic waves, the first apparatus determines the orientation of one apparatus relative to the other so that the drift of the gyroscope of each apparatus can be estimated. Determination of angle of arrival with antenna arrays can be performed with any technique known in the art, e.g. phase shift, time difference of arrival, etc.

The first apparatus receives measurements of the IMU of the second apparatus for establishing how the second apparatus is oriented since its orientation influences the orientation of the at least one antenna array of the second apparatus and, thus, it influences the first angle of arrival that is determined. Data about the planes in respect of which the first angle of arrival was measured is also received by the first apparatus; for example, data about the plane(s) may be provided (e.g. two vectors contained in each plane of measurement, a normal vector of each plane of measurement, angle formed by the plane and a horizontal or vertical plane, etc.), and/or data about the arrangement of the antennas in each antenna array may be provided, etc.

The first apparatus may also transmit the measurements of its IMU to the second apparatus; for instance, when the two apparatuses are part of a motion tracking system and the first apparatus is a motion tracker and the second apparatus is an apparatus that provides a motion sequence based on the measurements of the first apparatus and, preferably, other alike apparatuses that may be part of the system as well, and/or when the second apparatus is to perform the same processing described herein with regards to the first apparatus.

The first apparatus processes the received data and establishes the second angle of arrival when the first apparatus is arranged in such a way that said second angle of arrival is at least measurable with respect to the horizontal plane so that the effect of the drift in the heading (also referred to as azimuth in the present disclosure) of measurements of the IMU can be compensated for. To that end, the first angle of arrival is also processed when it was at least measurable with respect to the horizontal plane.

Once the first and second angles of arrival have been obtained, the first apparatus establishes the respective directions in the form of, for example, vectors, free vectors, angles, etc. These directions reflect the incoming direction of the electromagnetic waves each apparatus has captured from the other apparatus in their respective local frames. For a meaningful processing of these directions, they are converted into the global frame by applying respective transformations that depend upon the orientation of each apparatus. Then, the directions are projected onto a digitally created horizontal plane.

The estimation of the drift of the gyroscopes is then based on the fact that the relative orientation between the first and second apparatuses is the same for both; therefore, the directions that represent the relative orientations have to be identical but with opposed directions, that is to say, they have to be symmetrical. Therefore, the relative drift of the gyroscope or IMU of either apparatus can be estimated as the difference that exists between the projected direction of the angle of arrival that the apparatus determined and the projected direction of the other angle of arrival but in mirrored form, i.e. a symmetrical version of the projected direction of said other angle. The angle between these two projected directions is the estimated relative drift in the horizontal plane between the headings of the two apparatuses, namely, the angle is a drift affecting the heading that the gyroscope and/or IMU provides relative to the heading that the other apparatus' gyroscope and/or IMU provides.

In some embodiments, the method further comprises determining, by the first apparatus, when the at least one antenna array of the first apparatus is arranged to make the second angle of arrival of the one or more second data packets at least measurable with respect to a horizontal plane. Further, in these embodiments: the method further comprises determining, by the first apparatus, when the at least one antenna array of the second apparatus is arranged to make the first angle of arrival of the one or more second data packets at least measurable with respect to a horizontal plane; or the one or more second data packets further comprise an indication that the at least one antenna array of the second apparatus is arranged to make the first angle of arrival of the one or more second data packets at least measurable with respect to a horizontal plane.

The first apparatus processes its orientation and how the at least one antenna array is arranged therein to establish when the apparatus may measure the second angle of arrival with respect to the horizontal plane, that way the first apparatus avoids the computation of a drift estimate that will not allow an accurate correction of the heading error in measurements of the gyroscope and/or IMU. For instance, when the first and second apparatuses are one substantially above the other and with little or no distance between them in a horizontal plane, the angles of arrival will not be measured with respect to the horizontal plane due to, precisely, this arrangement of the two apparatuses. One or both apparatuses may check that they are not in such vertical arrangement by converting the direction of arrival into the global frame, and evaluating whether the direction is vertical or substantially vertical (e.g. the angle formed between said direction and a vertical vector is less than 2°, and/or 5°, and/or 10°, etc.), with the verticality being determined by e.g. having a direction similar to or parallel to the gravity vector as measured by e.g. the accelerometer.

The same processing can be conducted by the first apparatus with regards to the suitability of the second apparatus for measuring the first angle of arrival with respect to the horizontal plane; alternatively, the processing is conducted by the second apparatus, and an indication to that end is provided in the second data packet(s).

In some embodiments, the at least one antenna array of the first and/or second apparatuses is arranged to make an angle of arrival of packets wirelessly received at least measurable with respect to a horizontal plane when at least one of:

a linear combination of vectors defining a plane in respect of which each antenna array of the at least one antenna array of the respective apparatus may measure an angle of arrival of packets is such that can represent a vector defining the horizontal plane; and the at least one antenna array of the respective apparatus comprises three antenna arrays each of which is arranged such that the plane with which the angle of arrival of packets wirelessly received is measurable is orthogonal to the plane of the other antenna arrays of the same apparatus.

For the drift estimation in the horizontal plane so that the drift can be compensated for in heading measurements, the at least one antenna array of both apparatuses have to allow the measurement of the angle of arrival at least with respect to the horizontal plane.

This configuration exists at all times in some cases, which are when the at least one antenna array of the receiving apparatus has three different antenna arrays. Each of the three antenna arrays is arranged to make possible to measure the angle of arrival with respect to one of three perpendicular planes, hence irrespective of the orientation of the apparatus, angle of arrival can be determined with respect to the horizontal plane owing to the combination of two or three antenna arrays (depending on the orientation of the apparatus) or even owing to a single antenna array when it is measuring the angle of arrival relative to the horizontal plane (when the apparatus is upright, e.g. forming an angle with a global vertical axis that is between −5° and 5°, preferably as close to 0° as possible).

In some other cases the apparatus must process data in order to find out if the configuration is in place, which are when the at least one antenna array has one or two antenna arrays arranged to measure angle of arrival with respect to one or two perpendicular planes. The at least one antenna array is capable of measuring the angle with respect to the horizontal plane when the linear combination of the vectors of the planes in respect of which the angle of arrival is measurable can attain a vector that defines the horizontal plane. The apparatus or apparatuses have data about the arrangement of each antenna array so that the vectors of the plane(s) are determinable, and the apparatus or apparatuses also have the measurements of the IMU so that the horizontal plane is determinable. The configuration check for both apparatuses can be performed by the first apparatus, or each apparatus performs its own check; in the latter case, the first apparatus may receive an indication from the second apparatus that the first angle of arrival was determined when the configuration was in place, i.e. when the apparatus was in such condition that the angle of arrival was at least measurable with respect to the horizontal plane.

In some embodiments, the steps of wirelessly transmitting the one or more first data packets, wirelessly receiving the one or more second data packets, determining the second angle of arrival, providing the first and second directions, converting the first and second directions, projecting the first and second directions, and computing the first and/or second drift estimates are conducted a plurality of times to compute first and/or second drift estimates accounting for a cumulative drift error of the gyroscope or the IMU of the first and/or second apparatuses over time.

The repetition of the process a number of times allows frequent or substantially continuous drift estimation so that its error on the heading of measurements of the gyroscope or the IMU of either apparatus can be compensated for. Each time a new drift estimate is computed, the elapsed time between the transmission and reception of the first and second data packets is as low as possible, and/or one or both apparatuses are substantially still during the transmission and reception of said data packets, that way the drift(s) is estimated more accurately.

In some embodiments, the first apparatus at least computes the first drift estimate; and the method further comprises: correcting, by the first apparatus, a heading error introduced by a drift of its gyroscope or IMU by applying a drift compensation factor based on the most recently computed first drift estimate to each measurement provided by the gyroscope and/or the IMU.

Once the drift of the gyroscope or IMU has been estimated relative to the measurements of the gyroscope and/or IMU of the other apparatus, the first apparatus compensates for the heading error (that is to say, error in the orientation angle on the horizontal plane) by modifying the measurements of the gyroscope and/or the measurements of the IMU, which can be provided following the processing of the measurements of its sensor devices with a sensor fusion algorithm intended to improve the accuracy of the measurements as known in the art.

The correction of the heading error corresponds to a transformation that reduces the heading error or cancels it out. The transformation can be e.g. a constant value dependent upon the estimated drift that is summed to or subtracted from the measurements whose heading error is to be corrected. Said transformation is updated every time the drift of the gyroscope is estimated, thereby compensating for the heading error more accurately.

In some embodiments, a motion tracking system comprises the second apparatus and a plurality of the first apparatuses, each first apparatus is attached to a different body member of a user. In these embodiments, the method further comprises:

conducting the steps of wirelessly transmitting the one or more first data packets, wirelessly receiving the one or more second data packets, determining the second angle of arrival, providing the first and second directions, converting the first and second directions, projecting the converted first and second directions, and computing the first drift estimate in respect of each first apparatus of the plurality of first apparatuses;

measuring, by the IMU of each first apparatus of the plurality of first apparatuses, motion of the body member of the user having the respective first apparatus attached thereto;

wirelessly transmitting one or more third data packets from each first apparatus of the plurality of first apparatuses to the second apparatus, the one or more third data packets comprising data indicative of the motion of the respective body member; and determining, by the second apparatus, a motion of either the user or a plurality of body members of the user by processing the data of the one or more third data packets wirelessly received from the plurality of first apparatuses.

The motion tracking system allows a person to have the motion of her/his body members tracked in applications like machine-supervised physical rehabilitation. The second apparatus receives the measurements of the IMUs of the motion trackers, i.e. the plurality of first apparatuses, that are attached to body members of the person, and computes a motion tracking sequence with the received measurements. The second apparatus then compares the motion tracking sequence with e.g. a set of constraints associated with the concerned body members and movements to be performed by the person to assess whether the person is conducting the physical rehabilitation adequately. An exemplary assessment procedure is the one disclosed in WO2019243438A1, which is hereby incorporated by reference in its entirety.

Errors in the measurements might jeopardize the assessment because the resulting motion tracking sequence will reflect movements not actually performed by the person, so even if the person conducts the physical rehabilitation adequately, the second apparatus will not consider so, and possible guidance provided to the user for correction of her/his movements may lead the person to an incorrect performance of prescribed movements.

By correcting the heading errors in the measurements of the gyroscopes and/or IMUs, the orientation and movement of the concerned body members will be accurate with respect to the horizontal plane, thereby enabling a more accurate provision of a motion tracking sequence and comparison with the set of constraints and, consequently, reducing the risk that the person may get injured during physical rehabilitation.

In some embodiments, the first apparatus at least computes the second drift estimate. In these embodiments, the method further comprises wirelessly transmitting one or more data packets comprising the second drift estimate or a drift compensation factor based on the second drift estimate from the first apparatus to the second apparatus.

The first apparatus computes the drift estimate for the gyroscope or IMU of the second apparatus relative to the first apparatus, and sends it in that form or processed as a drift compensation factor that the second apparatus can apply to measurements of its gyroscope and/or IMU for correction of the heading error.

In some embodiments, the method further comprises: wirelessly receiving one or more third data packets at the first apparatus from the second apparatus, the one or more third data packets comprising: measurements of the IMU of the second apparatus with a heading error introduced by a drift of the gyroscope or IMU thereof corrected by applying a drift compensation factor based on the second drift estimate to each measurement provided by the gyroscope and/or the IMU.

Further IMU data provided by the second apparatus can be received with the heading error corrected so that the first apparatus can use more accurate measurements.

In some embodiments, the at least one antenna array of the first apparatus and/or the second apparatus comprises two or three antenna arrays, each antenna array of the two or three antenna arrays being arranged such that the plane with which the angle of arrival of packets wirelessly received is measurable is orthogonal to the plane of the other antenna arrays of the same apparatus.

The existence of two or three antenna arrays within an apparatus where the arrays are orthogonal one to each other (so that the planes for angle of arrival determination are orthogonal) increase the number of possible orientations of the apparatus(es) that the apparatus(es) may be for measuring angle of arrival at least with respect to the horizontal plane. With three orthogonal antenna arrays, any orientation of the apparatus(es) is possible for such angle of arrival measurement.

In some embodiments, the IMU of the first apparatus and/or the second apparatus has axes thereof defined by the respective accelerometer, and wherein the plane with which each antenna array of the at least one antenna array of the respective apparatus makes the angle of arrival measurable forms a predetermined angle with one of the axes of the IMU.

The antenna array(s) may not be aligned with the axes of the IMU of the respective apparatus, and thus form an angle with one of the axes that is greater than 0°. The antenna array arrangement data of the apparatuses indicates how the antenna array(s) within the apparatus, for example with reference to one of the axes of the IMU, so that the drift can be estimated in a precise manner.

In some embodiments, a time elapsed between:
the wireless transmission of the one or more first data packets, and
the wireless reception of the one or more second data packets or a wireless transmission of the one or more second data packets by the second apparatus,
is equal to or less than a predetermined time threshold.

In some embodiments, each of the one or more second data packets include further comprises a timestamp, and the first apparatus determines the second angle of arrival when the timestamp of the one or more second data packets of the wireless reception that the first apparatus processes for angle of arrival determination is such that a difference between the timestamp and a time when the first apparatus wirelessly transmitted the one or more first data packets is equal to or less than a predetermined time threshold.

The delay, i.e. elapsed time, between the transmission of the first and second data packets is to be as low as possible (e.g. 2 seconds, 1 second, 500 milliseconds, 100 milliseconds or even lower, etc.) for the drift estimation to be more accurate. With a lower delay, the transmission of the first and second data packets takes place closer in time, hence it is less likely that any one of the two apparatuses will have different position or orientation between the two transmissions.

In some embodiments, the method further comprises: synchronizing clocks of the first and second apparatuses, or modifying, by any one of the first and second apparatuses, a timestamp of data packets wirelessly transmitted and/or wireless received by any one of the first and second apparatuses.

Sometimes the clocks of the first and second apparatuses are not synchronized and have a relative time difference. These time differences influence the timestamps within the data packets. In the embodiments in which the processing conducted by the first apparatus is conditional on the timestamps, the lack of synchronization might cause that the first apparatus at least does not process the wireless packets it receives owing to an alleged delay that does not actually exist. Synchronization can be conducted by way of any technique known in the art, for example but without limitation, the technique described in EP3804420B1, which is hereby incorporated by reference in its entirety.

In some embodiments, the first apparatus and/or the second apparatus are/is still at least during a period of time comprising the steps of wirelessly transmitting the one or more first data packets and wirelessly receiving the one or more second data packets.

When either apparatus or both apparatuses remain still during the transmission and reception of the data packets that will be used for detecting the angle of arrival of the corresponding electromagnetic waves, the estimation of the drift can be more accurate as the angle of arrival is detectable when the two apparatuses are in the same or substantially the same positions, that is to say, the two apparatuses have been motionless or substantially motionless.

Another aspect of the disclosure relates to a method comprising:

wirelessly receiving one or more first data packets from a first apparatus at a second apparatus, each of the first and second apparatuses comprising:

at least one antenna array, each antenna array of the at least one antenna array being arranged to make an angle of arrival of packets wirelessly received at least measurable with respect to a respective plane;

and an inertial measurement unit, IMU, comprising both a gyroscope and an accelerometer;

determining, by the second apparatus, a first angle of arrival with which the second apparatus has wirelessly received the one or more first data packets, the first angle of arrival comprising angle information with respect to each plane that the at least one antenna array of the second apparatus makes the angle of arrival measurable;

wirelessly transmitting one or more second data packets from the second apparatus to the first apparatus, the one or more second data packets comprising: measurements of the IMU of the second apparatus, and the first angle of arrival; and wirelessly receiving one or more third data packets from the first apparatus at the second apparatus, the one or more third data packets comprising a drift estimate or a drift compensation factor for the gyroscope or IMU of the second apparatus relative to the first apparatus.

The second apparatus captures the electromagnetic waves that the first apparatus radiates for transmission of the one or more first data packets. The second apparatus determines the angle of arrival for those electromagnetic waves, and transmits that data to the first apparatus so that, the latter, can estimate the heading drift of the gyroscopes of either apparatus.

Further, the second apparatus can eventually receive the estimated heading drift from the first apparatus, or even a drift compensation factor for correcting its heading drift; in the case of the former, the second apparatus can compute the drift compensation factor to apply it as a correction to the measurements its gyroscope and/or IMU provides.

In some embodiments, the at least one antenna array of the first apparatus and/or the second apparatus comprises two or three antenna arrays, each antenna array of the two or three antenna arrays being arranged such that the plane with which the angle of arrival of packets wirelessly received is measurable is orthogonal to the plane of the other antenna arrays of the same apparatus.

In some embodiments, the IMU of the first apparatus and/or the second apparatus has axes thereof defined by the respective accelerometer, and wherein the plane with which each antenna array of the at least one antenna array of the respective apparatus makes the angle of arrival measurable forms a predetermined angle with one of the axes of the IMU.

Another aspect of the disclosure relates to a data processing apparatus comprising: at least one processor adapted to perform any of the methods disclosed herein; at least one antenna array, with each antenna array of the at least one antenna array arranged to make an angle of arrival of packets wirelessly received measurable with respect to a respective plane; and an inertial measurement unit, IMU, comprising both a gyroscope and an accelerometer.

Another aspect of the disclosure relates to an apparatus comprising: an inertial measurement unit comprising both a gyroscope and an accelerometer; at least one antenna array with each antenna array of the at least one antenna array arranged to make an angle of arrival of packets wirelessly received at least measurable with respect to a respective plane; and means adapted to execute the steps of any of the methods disclosed herein.

Another aspect of the disclosure relates to a motion tracking system comprising:

one first apparatus or a plurality of first apparatuses according to any of the apparatuses disclosed herein; and a plurality of second apparatuses when the system comprises one first apparatus, or one second apparatus when the system comprises a plurality of first apparatuses.

Further, each second apparatus comprises: an inertial measurement unit comprising both a gyroscope and an accelerometer, and at least one antenna array, each antenna array of the at least one antenna array being arranged to make an angle of arrival of packets wirelessly received at least measurable with respect to a respective plane. And each apparatus of the plurality of apparatuses (be it the plurality of first apparatuses or the plurality of second apparatuses) comprises means for attachment to a body member of a user.

The plurality of apparatuses is arrangeable or arranged on the body member of a user for motion tracking thereof. The measurements provided by the plurality of apparatuses, that is to say, the measurements provided by the IMU of each such apparatus, are transmittable to the single apparatus for processing thereof and provision of a motion tracking sequence. Further, the single apparatus may then compare the motion tracking sequence with a set of constraints to determine whether the body members of the user have been oriented and/or have moved correctly according to the constraints, thereby making it possible to conduct physical rehabilitation without supervision by a therapist.

Another aspect of the disclosure relates to a computer program product that has instructions which, when executed by a computing apparatus like e.g. any of the apparatuses disclosed herein, cause the computing apparatus to carry out the steps of a method according to the first aspect or the second aspect.

In some embodiments, the computer program product is embodied on a non-transitory computer-readable medium or a computer-readable data carrier has the computer program product stored thereon.

Another aspect of the disclosure relates to a data carrier signal carrying a computer program product according to any of the computer program products disclosed herein.

Another aspect of the disclosure relates to a method for computing drift estimation between inertial sensors, comprising: transmitting, wirelessly by a first inertial sensor, one or more first data packets to a second inertial sensor, wherein the one or more first data packets are received by the second inertial sensor according to a first angle of arrival; receiving, wirelessly by the first inertial sensor, one or more second data packets from the second inertial sensor, the one or more second data packets comprising angle of arrival data indicative of the first angle of arrival; determining, by the first inertial sensor, a second angle of arrival of the one or more second data packets received from the second inertial sensor; and computing, by the first inertial sensor, a drift estimate between the first inertial sensor and the second inertial sensor based at least on the first angle of arrival and the second angle of arrival, wherein the drift estimate is used to compensate for drift between the first inertial sensor and the second inertial sensor.

In some embodiments, the first inertial sensor and the second inertial sensor each comprise an inertial measurement unit (IMU) comprising both a gyroscope and an accelerometer. In some embodiments, further comprising correcting a heading error introduced by a drift of the gyroscope or IMU of the first inertial sensor or the second inertial sensor by applying a drift compensation factor based on the drift estimate to each measurement provided by the gyroscope and the IMU of the first inertial sensor or the second inertial sensor. In some embodiments, the drift estimate comprises at least one of a first drift estimate computed for the gyroscope or IMU of the first inertial sensor relative to the second inertial sensor or a second drift estimate computed for the gyroscope or IMU of the second inertial sensor relative to the first inertial sensor. In some embodiments, further comprising wirelessly transmitting, by the first inertial sensor, one or more data packets comprising the second drift estimate or a drift compensation factor based on the second drift estimate to the second inertial sensor. In some embodiments, further comprising wirelessly receiving, by the first inertial sensor, one or more third data packets from the second inertial sensor, the one or more third data packets comprising measurements of the IMU of the second inertial sensor with a heading error introduced by a drift of the IMU of the second inertial sensor that has been corrected by applying the drift compensation factor to the measurements provided by the IMU. In some embodiments, the first inertial sensor and the second inertial sensor each comprise at least one antenna array arranged to make an angle of arrival of packets wirelessly received measurable with respect to a respective plane. In some embodiments, further comprising determining when the at least one antenna array of the first inertial sensor is arranged to make the second angle of arrival of the one or more second data packets at least measurable with respect to a horizontal plane. In some embodiments, the one or more second data packets further comprise an indication that the at least one antenna array of the second inertial sensor is arranged to make the first angle of arrival of the one or more second data packets at least measurable with respect to a horizontal plane. In some embodiments, further comprising determine when the at least one antenna array of the second inertial sensor is arranged to make the first angle of arrival of the one or more second data packets at least measurable with respect to a horizontal plane. In some embodiments, computing the drift estimate comprises: providing a first direction of arrival based on the first angle of arrival and a second direction of arrival based on the second angle of arrival, and converting the first direction of arrival and the second direction of arrival into a global frame. In some embodiments, the first direction of arrival is converted into the global frame based on an orientation of the first inertial sensor, and wherein the second direction of arrival is converted into the global frame based on an orientation of the second inertial sensor. In some embodiments, further comprising projecting the first converted direction of arrival and the second converted direction of arrival onto a plane, wherein the drift estimate is based on the projected first direction and the projected second direction. In some embodiments, the drift estimate is based on a difference between the projected second direction and a mirrored projected first direction or a difference between the first projected direction and a mirrored second projected direction. In some embodiments, further comprising computing the drift estimate a plurality of times to account for a cumulative drift error over time of at least the first inertial sensor or the second inertial sensor. In some embodiments, the first inertial sensor determines the second angle of arrival when a difference between a timestamp of the one or more second data packets used to determine angle of arrival and a time when the first inertial sensor wirelessly transmitted the one or more first data packets is equal to or less than a predetermined time threshold. In some embodiments, the first inertial sensor comprises at least one antenna array arranged to make an angle of arrival of packets wirelessly received at least measurable with respect to a horizontal plane. In some embodiments, the at least one antenna array of the first inertial sensor comprises three antenna arrays each of which is arranged such that the plane with which the angle of arrival of packets wirelessly received is measurable is orthogonal to the plane of the other antenna arrays of the first inertial sensor.

Another aspect of the disclosure relates to a apparatus comprising: an inertial measurement unit (IMU) and at least one processor operative to: transmit wirelessly one or more first data packets to a second apparatus, wherein the one or more first data packets are received by the second apparatus according to a first angle of arrival; receive wirelessly one or more second data packets from the second apparatus, the one or more second data packets comprising angle of arrival data indicative of the first angle of arrival; determine a second angle of arrival of the one or more second data packets received from the second apparatus; and compute a drift estimate between the apparatus and the second apparatus based at least on the first angle of arrival and the second angle of arrival, wherein the drift estimate is used to compensate for drift between the apparatus and the second apparatus.

Another aspect of the disclosure relates to a motion tracking system comprising: at least one first inertial sensor configured for attachment to at least one body member of a user and a second inertial sensor, wherein the at least one first inertial sensor is operative to: transmit wirelessly one or more first data packets to the second inertial sensor, wherein the one or more first data packets are received by the second inertial sensor according to a first angle of arrival; receive wirelessly one or more second data packets from the second inertial sensor, the one or more second data packets comprising angle of arrival data indicative of the first angle of arrival; determine a second angle of arrival of the one or more second data packets received from the second inertial sensor; and compute a drift estimate between the at least one first inertial sensor and the second inertial sensor based at least on the first angle of arrival and the second angle of arrival, wherein the drift estimate is used to compensate for drift between the first inertial sensor and the second inertial sensor.

BRIEF DESCRIPTION OF THE DRAWINGS

To complete the description and in order to provide for a better understanding of the disclosure, a set of drawings is provided. Said drawings form an integral part of the description and illustrate embodiments of the disclosure, which should not be interpreted as restricting the scope of the disclosure, but just as examples of how the disclosure can be carried out. The drawings comprise the following figures.

DETAILED DESCRIPTION

Figure 1:
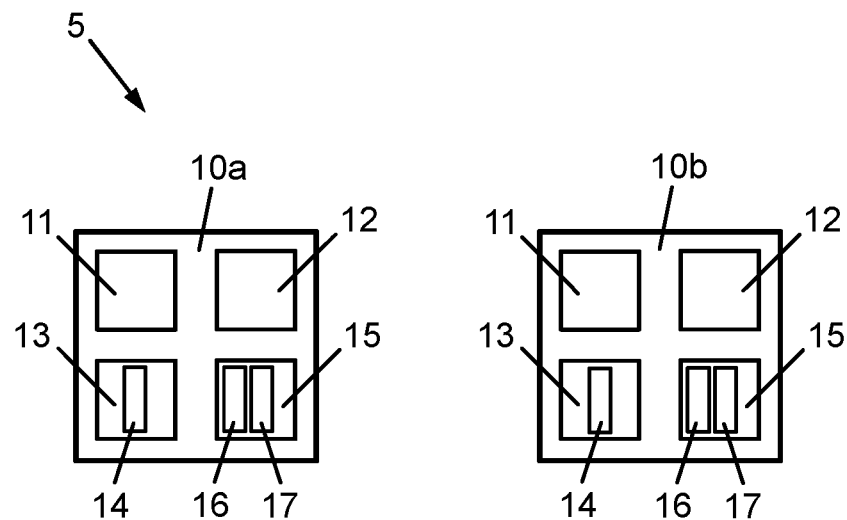
FIG. 1 shows a system in accordance with embodiments.

FIG. 1 shows a system 5 in accordance with embodiments, for example a motion tracking system. The system 5 includes first and second apparatuses 10a, 10b, which may be identical or different. For example, the first apparatus 10a may be a motion tracking device, and the second apparatus may be a tablet, a mobile phone, a personal computer, etc.

Both apparatuses 10a, 10b include at least one processor 11, at least one memory 12, a wireless communications module 13 for radiofrequency signal transmission and reception, and an IMU 15. The wireless communications modules 13 include at least one antenna array 14 whereby electromagnetic waves are captured and radiated. The inertial measurement units 15 include inertial sensors, for example a gyroscope 16 and an accelerometer 17. The at least one memory 12 of the apparatuses 10a, 10b may have instructions and/or a computer program stored therein that, upon execution by the at least one processor 11, enable the apparatus 10a, 10b to estimate the drift of the IMU 15 or gyroscope 16 of one of the apparatuses 10a, 10b relative to the measurements of the other one of the apparatuses 10b, 10a.

Although not illustrated, in some embodiments, any one of or both of apparatuses 10a, 10b include an attaching device for attachment to body members of a person, e.g. straps, Velcro, etc.

Figure 2:
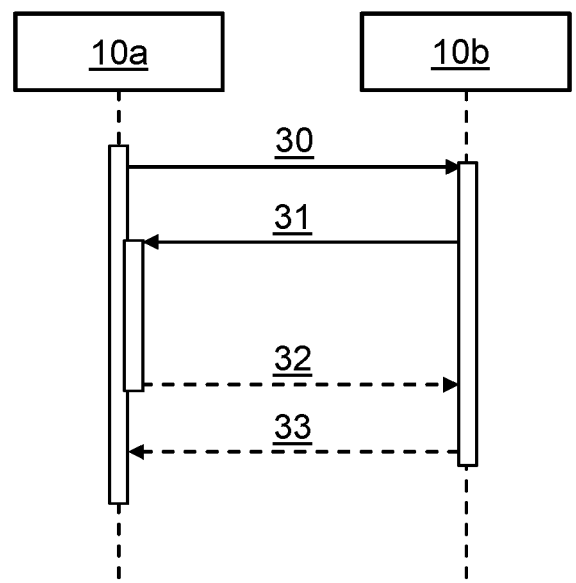
FIG. 2 shows a transaction diagram corresponding to the implementation of methods in accordance with embodiments.

FIG. 2 shows a transaction diagram corresponding to the implementation of methods in accordance with embodiments. The diagram shows the exchange of data packets between first and second apparatuses 10a, 10b, like those described with reference to FIG. 1.

The first apparatus 10a wirelessly transmits 30 at least one data packet to the second apparatus 10b. The at least one data packet can include measurements of the IMU of the first apparatus 10a, or be an advertisement package with data that identifies the first apparatus 10a, or be a handshaking package, etc. The second apparatus 10b receives the transmission and detects the angle of arrival of the same with the at least one antenna array it has, and when the measurable angle of arrival at least comprises an angle with respect to a horizontal plane.

The second apparatus 10b wirelessly transmits 31, to the first apparatus 10a, at least one data packet with measurements of the IMU of the second apparatus 10b and the angle of arrival that it detected.

The first apparatus 10a detects the angle of arrival of the wireless transmission 31 it received when the measurable angle of arrival at least comprises an angle with respect to a horizontal plane.

By way of example only, the first and second apparatuses 10a, 10b might wirelessly communicate over a Bluetooth v. 5.1 (or subsequent version) wireless communication that has angle of arrival detection already incorporated therein. It is noted, however, that any other wireless communication standard could be used as well.

Then, the first apparatus 10a digitally processes both angles of arrival together with the measurements of the IMUs of both apparatuses 10a, 10b, for example as explained next with reference to FIGS. 3A-3C and 4, to estimate a drift of the gyroscope or IMU of the first apparatus 10a and/or a drift of the gyroscope or IMU of the second apparatus 10b. When the drift is estimated at least for the gyroscope or IMU of the second apparatus 10b, the same may be wirelessly transmitted 32 (shown with a dashed arrow to illustrate that it takes place in some embodiments) in at least one data packet to the second apparatus 10b, or be transmitted 32 processed as a drift compensation factor. Subsequent wireless transmissions 33 (shown with a dashed arrow to illustrate that it takes place in some embodiments) of the second apparatus 10b to the first apparatus 10a may then include measurements of its IMU with the heading error reduced or cancelled.

Figure 3A:
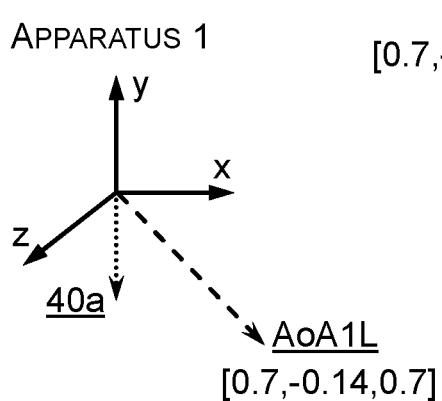
FIGS. 3A-3C show directions resulting from angle of arrival determinations and projections thereof onto a horizontal plane for estimation of drift of gyroscopes as performed in methods in accordance with embodiments.

FIG. 3A shows a direction of arrival AoA1L (shown with a dashed line for clarity reasons only) corresponding to the wireless transmission, at a first apparatus 10a, of at least one data packet from a second apparatus 10b; for example, wireless transmission 31 of FIG. 2. The direction of arrival AoA1L is provided with respect to a horizontal plane as determined by the first apparatus 10a, which the apparatus can establish from a direction of gravity 40a (shown with a dotted line for clarity reasons only) measured by its IMU that includes an accelerometer. Direction AoA1L is in the local frame of the first apparatus 10a.

Figure 3C:
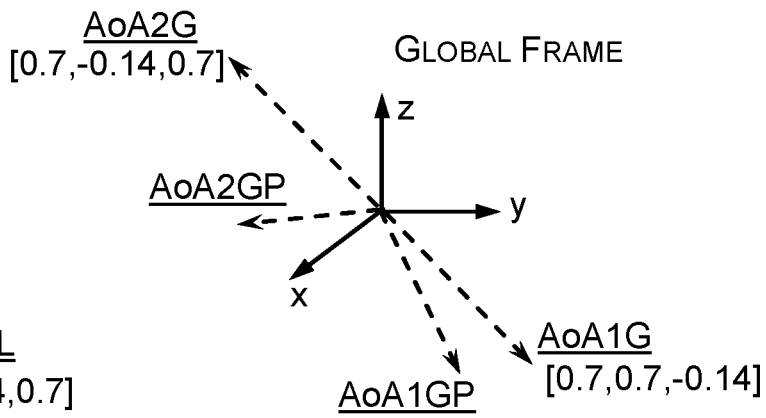
Figure 3B:
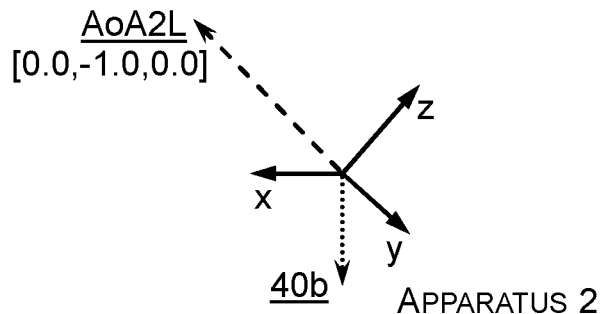

FIG. 3B shows a direction of arrival AoA2L (shown with a dashed line for clarity reasons only) corresponding to the opposite wireless transmission, i.e. a transmission received at the second apparatus 10b from the first apparatus 10a; for example, wireless transmission 30 of FIG. 2. The direction of arrival AoA2L is provided with respect to a horizontal plane as determined by the second apparatus 10b, which the apparatus can establish from a direction of gravity 40b (shown with a dotted line for clarity reasons only) measured by its IMU that includes an accelerometer. Direction AoA2L is in the local frame of the second apparatus 10b.

As it can be appreciated from FIGS. 3A-3B, AoA1L and AoA2L seem to be symmetrical (as it should be the case due to the corresponding relative orientations of the two apparatuses), but the local axes of the represented directions AoA1L, AoA2L do not match. Hence, conversion into a global frame is necessary.

FIG. 3C shows both directions AoA1G and AoA2G (both shown with dashed lines for clarity reasons only) converted into the global frame as processed by e.g. the first apparatus. The first apparatus takes into account the orientations as provided by the IMUs, particularly the rotation matrices thereof, of each apparatus for transformation of the respective direction into the global frame.

Once the directions AoA1G and AoA2G have been obtained, the apparatus projects those directions onto a horizontal plane, as shown in FIG. 3C, by way of projected directions AoA1GP and AoA2GP (both shown with dashed lines for clarity reasons only). The horizontal plane is defined by the x and y axes of the global frame.

All the directions represented in FIGS. 3A-3C are three-dimensional vectors (or two-dimensional vectors in the case of directions AoA1GP and AoA2GP if defined with regards to the horizontal plane), but it will be readily apparent that a different entity could be used instead as directions without departing from the scope of the present disclosure.

Figure 4:
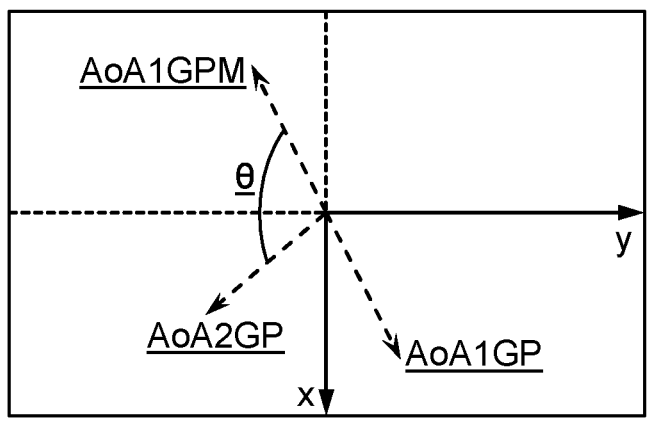
FIG. 4 shows how the drift is estimated following the projections of FIG. 3C as performed in methods in accordance with embodiments.

For the estimation of the drift, reference is made to FIG. 4, which shows the horizontal plane x-y in two dimensions with the two projected directions AoA1GP and AoA2GP of FIG. 3C. The horizontal plane is defined by the global z vector, which can be retrieved from e.g. a gravity acceleration measured by the IMU of the respective apparatus.

In the example shown in FIG. 4, the drift of the gyroscope or IMU of the second apparatus is being estimated relative to the heading of the gyroscope or IMU of the first apparatus. For that, the first apparatus provides a symmetrical or mirrored version of the projected direction corresponding to the angle of arrival determined by the first apparatus, thereby providing direction AoA1GPM; the symmetry or mirroring is with respect to the origin of the axes illustrated.

If the gyroscope or IMU of the second apparatus had no drift relative to the heading provided by the first apparatus, the directions AoA2GP and AoA1GPM (shown with a dashed line for clarity reasons only) would be parallel and with the same direction due to the symmetry of the directions corresponding to the angles of arrival. However, when there is drift, like in the present example, an angle θ is formed between directions AoA2GP and AoA1GPM. The angle θ is the drift in the horizontal plane, i.e. the heading or azimuth error.

The estimated drift can then be used for compensation of the heading error, for example by adding or subtracting (depending on the direction taken for measuring the angle) angle θ to the measurements of the gyroscope or IMU of the respective apparatus.

For estimating the drift of the first apparatus, the symmetrical or mirrored version of direction AoA2GP is provided, and the difference between direction AoA1GP and the mirrored version of direction AoA2GP is measured.

It is noted that when a plurality of first apparatuses or a plurality of second apparatuses is arranged and the described process is conducted for each such apparatus of the plurality, the drift in the measurements of the gyroscope or IMU of all the apparatuses of the plurality can be estimated and compensated for relative to the same other apparatus. Therefore, any measurements exchanged between the plurality of first apparatuses and the second apparatus, or between the plurality of second apparatuses and the first apparatus will have a known or compensated drift in the azimuth of the measurements relative to the apparatuses at the receiving end of the measurements exchange.

Figure 5:
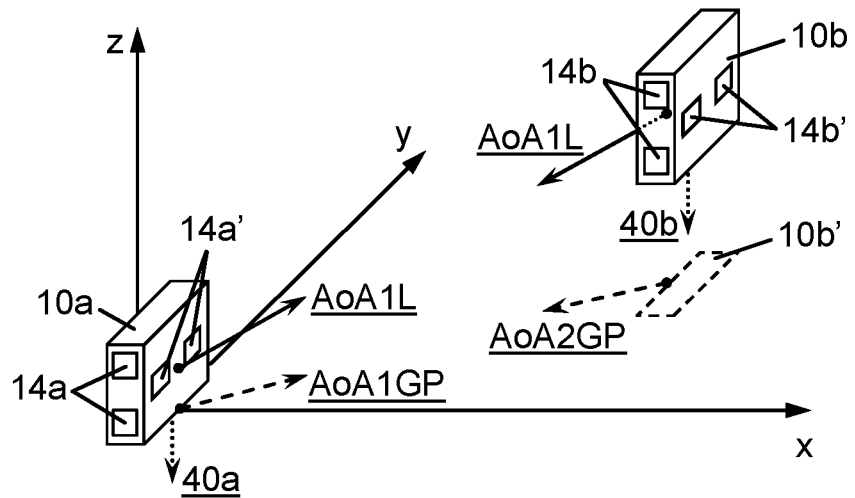
FIG. 5 shows two apparatuses wirelessly communicating and detecting respective angles of arrival as performed in methods in accordance with embodiments.

FIG. 5 shows two apparatuses 10a, 10b wirelessly communicating and detecting respective angles of arrival as performed in methods in accordance with embodiments.

For the sake of the illustration only, a set of Cartesian coordinates has been represented, with the origin being located at some predetermined point of the first apparatus 10a; any other coordinate representation could be possible as well without departing from the scope of the present disclosure. The first apparatus 10a thus lies on all three planes x-y, y-z and x-z. The second apparatus 10b, which is a remote apparatus apart from the first apparatus 10a, has its footprint 10b' (shown with dashed lines for clarity reasons only) represented on the horizontal plane x-y. For the sake of simplicity only, the two apparatuses 10a, 10b are identically oriented, but at other times or in other embodiments, the two apparatuses 10a, 10b are differently oriented.

The first apparatus 10a has a first antenna array 14a and a second antenna array 14a'. In this example, the two antenna arrays 14a, 14a' are arranged on the first apparatus 10a such that each enables measurements of angle of arrival at least with respect to a plane orthogonal to a measurement plane of the other antenna array, which even if preferable is not a requirement. The same is true for the second apparatus 10b, which has respective first and second antenna arrays 14b, 14b'. In this example, each antenna array 14a, 14a', 14b, 14b' includes two antennas, but more antennas would be possible as well; likewise, the antenna arrays of each apparatus 10a, 10b might comprise a different number of antennas.

Angles or directions of arrival AoA1L and AoA2L of electromagnetic waves captured by the respective apparatuses 10a, 10b are shown. Said angles are in the local frame of each apparatus 10a, 10b, but given the orientations of the apparatuses, the angles could be regarded as being in a global frame. An azimuth of the angles of arrival AoA1L and AoA2L is also represented by way of directions AoA1GP and AoA2GP (shown with dashed lines for clarity reasons only), which are the angles or directions of arrival AoA1L and AoA2L converted into the global frame and then projected onto the horizontal plane x-y.

The directions AoA1GP and AoA2GP, i.e. the azimuths, can then be used by e.g. the first apparatus 10a to estimate the relative drift between the measurements.

Figure 6:
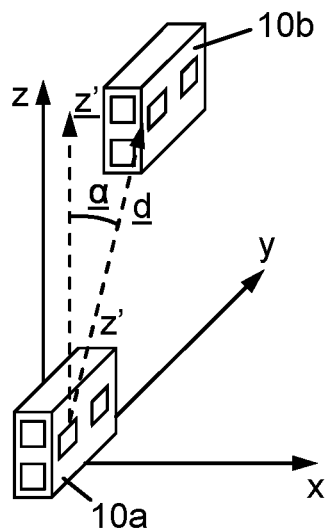
FIG. 6 shows a limit relative location of two apparatuses in some exemplary embodiments.

FIG. 6 shows a limit relative location of two apparatuses 10a, 10b in some exemplary embodiments. In particular, the two apparatuses 10a, 10b are preferably not one on top of the other, and preferably there is some gap in a horizontal direction (a direction contained in the horizontal plane x-y).

In this sense, preferably an angle α is formed between a vertical direction or vector z', and a vector or segment d (for example, a minimum distance segment) with endpoints at predetermined points of the first and second apparatuses 10a, 10b, with an absolute value of the angle α being equal to or greater than a predetermined minimum angle, e.g. 2°, 5°, or greater. The greater the angle α, the more accurate the relative drift that an apparatus will estimate.

In this text, the term "includes", "comprises" and its derivations (such as "including", "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for computing drift estimation between inertial sensors, comprising:
   transmitting, wirelessly by a first inertial sensor, one or more first data packets to a second inertial sensor, wherein the one or more first data packets are received by the second inertial sensor according to a first angle of arrival;
   receiving, wirelessly by the first inertial sensor, one or more second data packets from the second inertial sensor, the one or more second data packets comprising angle of arrival data indicative of the first angle of arrival;
   determining, by the first inertial sensor, a second angle of arrival of the one or more second data packets received from the second inertial sensor; and
   computing, by the first inertial sensor, a drift estimate between the first inertial sensor and the second inertial sensor based at least on the first angle of arrival and the second angle of arrival, wherein the drift estimate is used to compensate for drift between the first inertial sensor and the second inertial sensor.

2. The method of claim 1, wherein the first inertial sensor and the second inertial sensor each comprise an inertial measurement unit (IMU) comprising both a gyroscope and an accelerometer.

3. The method of claim 2, further comprising correcting a heading error introduced by a drift of the gyroscope or IMU of the first inertial sensor or the second inertial sensor by applying a drift compensation factor based on the drift estimate to each measurement provided by the gyroscope and the IMU of the first inertial sensor or the second inertial sensor.

4. The method of claim 3, wherein the drift estimate comprises at least one of a first drift estimate computed for the gyroscope or IMU of the first inertial sensor relative to the second inertial sensor or a second drift estimate computed for the gyroscope or IMU of the second inertial sensor relative to the first inertial sensor.

5. The method of claim 4, further comprising wirelessly transmitting, by the first inertial sensor, one or more data packets comprising the second drift estimate or a drift compensation factor based on the second drift estimate to the second inertial sensor.

6. The method of claim 5, further comprising wirelessly receiving, by the first inertial sensor, one or more third data packets from the second inertial sensor, the one or more third data packets comprising measurements of the IMU of the second inertial sensor with a heading error introduced by a drift of the IMU of the second inertial sensor that has been corrected by applying the drift compensation factor to the measurements provided by the IMU.

7. The method of claim 1, wherein the first inertial sensor and the second inertial sensor each comprise at least one antenna array arranged to make an angle of arrival of packets wirelessly received measurable with respect to a respective plane.

8. The method of claim 7, further comprising determining when the at least one antenna array of the first inertial sensor is arranged to make the second angle of arrival of the one or more second data packets at least measurable with respect to a horizontal plane.

9. The method of claim 8, wherein the one or more second data packets further comprise an indication that the at least one antenna array of the second inertial sensor is arranged to make the first angle of arrival of the one or more second data packets at least measurable with respect to a horizontal plane.

10. The method of claim 8, further comprising determining when the at least one antenna array of the second inertial sensor is arranged to make the first angle of arrival of the one or more second data packets at least measurable with respect to a horizontal plane.

11. The method of claim 1, wherein computing the drift estimate comprises: providing a first direction of arrival based on the first angle of arrival and a second direction of arrival based on the second angle of arrival, and converting the first direction of arrival and the second direction of arrival into a global frame.

12. The method of claim 11, wherein the first direction of arrival is converted into the global frame based on an orientation of the first inertial sensor, and wherein the second direction of arrival is converted into the global frame based on an orientation of the second inertial sensor.

13. The method of claim 11, further comprising projecting the first converted direction of arrival and the second converted direction of arrival onto a plane, wherein the drift estimate is based on the projected first direction and the projected second direction.

14. The method of claim 13, wherein the drift estimate is based on a difference between the projected second direction and a mirrored projected first direction or a difference between the first projected direction and a mirrored second projected direction.

15. The method of claim 1, further comprising computing the drift estimate a plurality of times to account for a cumulative drift error over time of at least the first inertial sensor or the second inertial sensor.

16. The method of claim 1, wherein the first inertial sensor determines the second angle of arrival when a difference between a timestamp of the one or more second data packets used to determine angle of arrival and a time when the first inertial sensor wirelessly transmitted the one or more first data packets is equal to or less than a predetermined time threshold.

17. The method of claim 1, wherein the first inertial sensor comprises at least one antenna array arranged to make an angle of arrival of packets wirelessly received at least measurable with respect to a horizontal plane.

18. The method of claim 17, wherein the at least one antenna array of the first inertial sensor comprises three antenna arrays each of which is arranged such that the plane with which the angle of arrival of packets wirelessly received is measurable is orthogonal to the plane of the other antenna arrays of the first inertial sensor.

19. An apparatus comprising:
an inertial measurement unit (IMU) and at least one processor operative to:
transmit wirelessly one or more first data packets to a second apparatus, wherein the one or more first data packets are received by the second apparatus according to a first angle of arrival;
receive wirelessly one or more second data packets from the second apparatus, the one or more second data packets comprising angle of arrival data indicative of the first angle of arrival;
determine a second angle of arrival of the one or more second data packets received from the second apparatus; and
compute a drift estimate between the apparatus and the second apparatus based at least on the first angle of arrival and the second angle of arrival, wherein the drift estimate is used to compensate for drift between the apparatus and the second apparatus.

20. A motion tracking system comprising:
at least one first inertial sensor configured for attachment to at least one body member of a user and a second inertial sensor, wherein the at least one first inertial sensor is operative to:
transmit wirelessly one or more first data packets to the second inertial sensor, wherein the one or more first data packets are received by the second inertial sensor according to a first angle of arrival;
receive wirelessly one or more second data packets from the second inertial sensor, the one or more second data packets comprising angle of arrival data indicative of the first angle of arrival;
determine a second angle of arrival of the one or more second data packets received from the second inertial sensor; and
compute a drift estimate between the at least one first inertial sensor and the second inertial sensor based at least on the first angle of arrival and the second angle of arrival, wherein the drift estimate is used to compensate for drift between the first inertial sensor and the second inertial sensor.

* * * * *